United States Patent [19]

Hahn et al.

[11] Patent Number: 5,002,808

[45] Date of Patent: Mar. 26, 1991

[54] ADHESION METHODS EMPLOYING BENZOCYCLOBUTENE-BASED ORGANOSILANE ADHESION AIDS

[75] Inventors: Stephen F. Hahn; Dennis J. Kreil, both of Midland, Mich.

[73] Assignee: The Dow Chemical Company, Midland, Mich.

[21] Appl. No.: 307,813

[22] Filed: Feb. 8, 1989

Related U.S. Application Data

[62] Division of Ser. No. 172,060, Mar. 23, 1988, Pat. No. 4,831,172.

[51] Int. Cl.$^5$ ............................................. B05D 3/02
[52] U.S. Cl. .................................. 427/387; 106/287.13; 106/287.16; 156/307.3; 156/314; 427/333; 427/400; 427/402; 428/420

[58] Field of Search .......................... 156/307.3, 314; 427/333, 402, 400, 387; 106/287.13, 287.16; 428/420

[56] References Cited

U.S. PATENT DOCUMENTS

| | | | |
|---|---|---|---|
| 3,481,815 | 12/1969 | Barry et al. | 156/307.3 |
| 3,788,895 | 1/1974 | Schimmer et al. | 427/333 |
| 4,118,540 | 10/1978 | Amort et al. | 427/387 |
| 4,759,874 | 7/1988 | Gros | 156/307.3 |

*Primary Examiner*—John J. Gallagher
*Attorney, Agent, or Firm*—Charles J. Enright

[57] ABSTRACT

Benzocyclobutene-functionalized organosilanes, and a method of increasing adhesion between a polymer and an inorganic surface by using benzocyclobutene-functionalized organosilanes as adhesion aids.

28 Claims, No Drawings

ADHESION METHODS EMPLOYING BENZOCYCLOBUTENE-BASED ORGANOSILANE ADHESION AIDS

This is a division of application Ser. No. 07/172,060, filed Mar. 23, 1988, now U.S. Pat. No. 4,831,172.

BACKGROUND OF THE INVENTION

This invention relates to adhesion aids for increasing the adhesion of polymers to inorganic surfaces and the methods for increasing this adhesion. More specifically, the invention relates to benzocyclobutene-functional silanes and their use as adhesion aids.

Adhesion of polymers to inorganic surfaces is often a critical factor in the reliability of the polymer for the desired application. For example, in the aerospace industry, a polymer matrix frequently bonds two metal surfaces. Inadequate bond strength can lead to catastrophic failure. In the electronics industry, "die attach" adhesives are necessary to bond the inactive side of a semiconductor chip to the electronic package. Bond strength is also important for materials used as insulating layers in multilayered electronic devices. Polymers are replacing inorganic materials for these and other electronic applications because of may desirable properties, such as low dielectric constant, low moisture pickup, and unique fabrication opportunities. Without adequate bond strength, the polymer is a poor candidate for replacing standard inorganic materials.

By far the most prevalent and widely studied adhesion aids for increasing the adhesion of polymers to inorganic surfaces are the organosilanes (see, for example, the comprehensive work on organosilanes in Plueddemann, *Silane Coupling Agents,* Plenum Press, 233 Spring Street, New York, N.Y. (1982)). Organosilanes improve adhesion by forming a bond between the polymer matrix and the inorganic surface, and by increasing the ability of the resin to "wet" the surface before cure. Although the particular mechanism by which bonding occurs is uncertain, it is believed that the silane group of the organosilane couples with the surface via hydrolysis and the chosen organic functionality of the organosilane reacts with the polymer matrix. Surface wetting of the resin on the inorganic surface is believed to be generally improved by providing a moisture-free surface.

A catalog published by Petrarch Systems, Inc. (Bristol, Pa.), entitled "Silicon Compounds", 1984, disclosed at pages 71-74 silane coupling agent chemistry and a guide for selecting coupling agents for different thermosets and thermoplastics. Although a number of different coupling agents are disclosed for varying applications, the development of new polymeric systems for aerospace and electronics applications, such as those described above, prompts the need for new organosilane coupling agents. In particular, an organosilane adhesion aid improving adhesion between an inorganic surface and polymers derived from benzocyclobutene (BCB) is desired. BCB-derived polymers are based on relatively new technology and offer outstanding thermal stability at high temperatures, solvent resistance and low dielectric constants (see, for example, U.S. Pat. No. 4,540,763). An organosilane coupling agent that could effectively improve the adhesion of BCB-derived polymers would greatly enhance the utility of the polymers.

SUMMARY OF THE INVENTION

In one aspect, the invention is an organosilane adhesion aid represented by the formula:

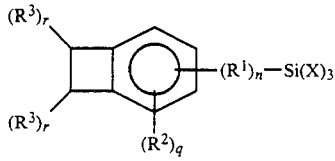

wherein
$R^1$ is —CH=CH—Y— or

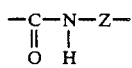

and
Y is a direct bond, phenylene or $(CH_2)_m$,
Z is phenylene or $(CH_2)_m$;
m is an integer between 1 and 4, inclusive;
$R^2$ is $C_{1-4}$ alkyl, methoxy, methoxycarbonyl, trifluoromethoxycarbonyl, nitro, or halo;
each $R^3$ is independently $C_{1-4}$ alkyl, halo, nitro, or cyano;
X is $C_{1-4}$ alkoxy;
n is 0 or 1; and
each q and r is independently 0 or 1.

In another aspect, the invention is a method of increasing adhesion between an inorganic surface and a polymer. The method comprises:

(a) dissolving in an effective amount of an organosilane adhesion aid of the formula

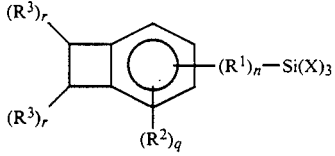

wherein
$R^1$ is —CH=CH—Y— or

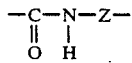

and
Y is a direct bond, phenylene or $(CH_2)_m$,
Z is phenylene or $(CH_2)_m$;
m is an integer between 1 and 4, inclusive;
$R^2$ is $C_{1-4}$ alkyl, methoxy, methoxycarbonyl, trifluoromethoxycarbonyl, nitro, or halo;
each $R^3$ is independently $C_{1-4}$ alkyl, halo, nitro, or cyano;
X is $C_{1-4}$ alkoxy;
n is zero or 1; and
each q and r is independently zero or 1; in a suitable solvent so as to prepare a solution, (b) applying an amount of the solution to the inorganic surface sufficient to wet the surface, (c) removing substantially all of the solvent from the applied solution, (d) contacting a monomer or prepolymer precursor of the polymer with the wetted inorganic surface, and then (e) polymerizing the monomer of prepolymer while maintaining contact between the monomer or prepolymer and the wetted inorganic surface.

Alternatively, the method comprises:

(a) contacting the inorganic surface with a homogeneous mixture of a monomer or prepolymer precursor of the polymer and an effective amount of an organosilane adhesion aid of the formula:

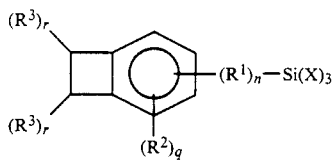

wherein
R$^1$ is —CH=CH—Y— or

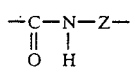

and
Y is a direct bond, phenylene or (CH$_2$)$_m$,
Z is phenylene or (CH$_2$)$_m$;
m is an integer between 1 and 4, inclusive;
R$^2$ is C$_{1-4}$ alkyl, methoxy, methoxycarbonyl, trifluoromethoxycarbonyl, nitro, or halo;
each R$^3$ is independently C$_{1-4}$ alkyl, halo, nitro, or cyano;
X is C$_{1-4}$ alkoxy;
n is 0 or 1; and
each q and r is independently 0 or 1; and then (b) polymerizing the monomer or prepolymer while maintaining contact between the mixture and the inorganic surface.

The organosilane adhesion aid of this invention increases adhesion of polymers to inorganic surfaces relative to the adhesion achieved without using such an adhesion aid. The BCB functionality of the organosilane reacts readily with numerous polymeric systems to promote a stable bond between the inorganic surface and the polymer matrix, particularly when the polymer matrix is derived from a BCB monomer or prepolymer.

The organosilane adhesion aid of this invention is useful for all applications where adhesion of a polymer to an inorganic surface is an important polymer property. These applications include, for example, the use of polymers as die attach adhesives, insulating and planarization layers for multilayer electronic devices, for encapsulation of electronic packages, and for bonding metal surfaces.

DETAILED DESCRIPTION OF THE INVENTION

The organosilane adhesion aids described in this specification are BCB-functional silanes and will be referred to throughout as BCB-silanes. The BCB-silanes can be represented by the following formula:

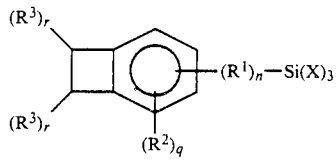

wherein
R$^1$ is —CH=CH—Y— or

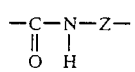

and
Y is a direct bond, phenylene or (CH$_2$)$_m$,
Z is phenylene of (CH$_2$)$_m$;
m is an integer between 1 and 4, inclusive;
R$^2$ is C$_{1-4}$ alkyl, methoxy, methoxycarbonyl, trifluoromethoxycarbonyl, nitro, or halo;
each R$^3$ is independently C$_{1-4}$ alkyl, halo, nitro, or cyano;
X is C$_{1-4}$ alkoxy;
n is 0 of 1; and
each q and r is independently 0 or 1

The preferred substituent on the cyclobutane ring of the BCB group is halo, preferably chloro. The preferred substituents on the benzene ring of the BCB group are methyl, methoxy, or halo. Preferably, both the cyclobutane and benzene rings of the BCB group are unsubstituted. Preferred alkoxy for the silane group is methoxy or ethoxy. The most preferred BCB-silanes are represented by the following formulas:

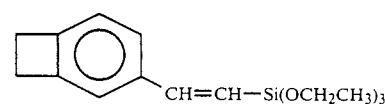
(I)

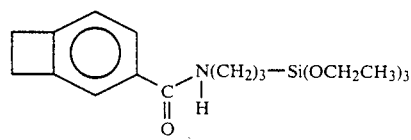
(II)

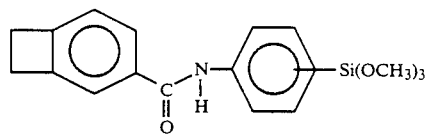
(III)

In a preferred embodiment of this invention, the BCB-silane bonds a polymer to an inorganic surface when the BCB-silane is contacted with the inorganic surface and either a monomer precursor of the chosen polymer of a prepolymer precursor of the chosen polymer during cure. Elevated temperatures, typically greater than 200° C., activate the cyclobutane ring of the BCB-silane by opening the ring to form a conjugated diene (ortho-quinodimethane). The activated ring can potentially react with any dienophile via a Diels-Alder reaction as disclosed in Feiser and Feiser, *Organic Chemistry*, 3rd ed., (1980). In this manner, the activated cyclobutane ring can react with dienophilic functionalities which the monomer or prepolymer possesses. As a result, the cyclobutane ring can react directly with the monomer or prepolymer as it is being cured, thus effectively bonding the BCB-silane to the desired polymer.

Although the BCB-silane can potentially react with any dienophile, a preferred dienophile is one formed from the activation of another cyclobutane ring on a BCB group. Therefore, preferred polymers used in conjunction with BCB-silanes are derived from monomers or prepolymers having at least one BCB group. These monomers and prepolymers are described in U.S. Pat. Nos. 4,540,763 and 4,642,329; and copending U.S. application Ser. No. 835,013, filed Feb. 28, 1986 and U.S. Ser. No. 132,734, filed Dec. 14, 1987. Each of these patents and copending applications are incorporated by reference herein. The most preferred polymers are derived from monomers represented by the following formulas:

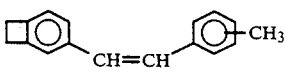 (IV)

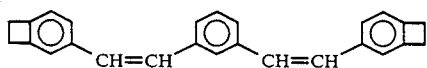 (V)

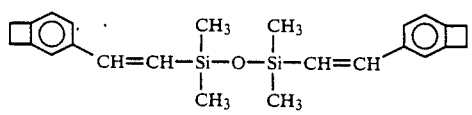 (VI)

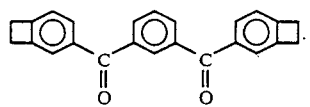 (VII)

For purposes of describing this invention, the following numbering system will be used to designate substitution on BCB:

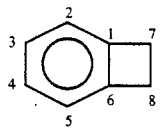

The BCB-silanes of this invention can be prepared by coupling known silanes with a BCB. For example, substantially equimolar amounts of a vinyl-functional trialkoxysilane and 3-bromobenzocyclobutene can be reacted using the process conditions disclosed in U.S. Pat. No. 3,922,299 (Heck). The Heck patent describes coupling aryl halides with olefinic compounds having at least one hydrogen on a vinylic position. The coupling reaction occurs in the presence of a Group VIII metal, a trivalent arsenic or phosphorous compound, and a soluble trialkylamine. The preferred Group VIII metal is palladium. Preferably, the reaction is carried out in the presence of a suitable nonreacting diluent, such as acetonitrile, to control the reaction temperature during the exothermic reaction.

A another example, substantially equimolar amounts of an amino-functional trialkoxysilane and benzocyclobutene-3-acid chloride can be reacted in the presence of a suitable nonreacting diluent, such as toluene or methylene chloride, and an acid scavenger, such as a tertiary amine. Preferably, the reaction temperature is maintained below 20° C.

The method of applying the BCB-silane does not differ from the methods of applying conventional silane coupling agents. These methods are well known in the art. A good description of alternative methods is outlined in the catalog offered by Petrarch Systems, Inc., entitled "Silicon Compounds", supra, at page 75, which is incorporated by reference herein.

Typically, the method of application is controlled by whether the monomer or prepolymer is a solid or a liquid. If the monomer or prepolymer is a liquid, the BCB-silane can be easily mixed directly with the monomer or prepolymer and then applied to the inorganic surface for curing. Preferably, the amount of BCB-silane in the mixture ranges from about 0.01 to about 20 percent by weight of the mixture. Alternatively, a solid monomer or prepolymer can be dissolved in a suitable organic solvent so that the BCB-silane can be mixed directly with the solution.

When the monomer or prepolymer is a solid, it is often most convenient to dissolve the BCB-silane in a suitable solvent and then to apply the BCB-silane solution to the inorganic surface. Preferably, the solvent is either a $C_{1-4}$ alcohol/water mixture or an organic solvent. Preferred $C_{1-4}$ alcohols are methanol and ethanol. Examples of suitable organic solvents are xylene, tetrahydrofuran (THF), toluene, heptane, hexane, acetone, and methylene chloride. The preferred organic solvents are xylene and THF. The amount of BCB-silane in solution desirably ranges from about 0.1 to about 1 percent by weight of solution. After the BCB-silane solution is applied, the solvent can then be removed and the treated surface can be coated with the monomer or prepolymer for cuing. Alternatively, the monomer or prepolymer can be dissolved in a suitable organic solvent, such as xylene, THF, and toluene, before being applied to the treated surface. The most preferred organic solvents for dissolving the monomer or prepolymer are xylene and THF.

The inorganic surfaces within the scope of this invention include any inorganic surface that can interact or bond with a silane. Included within this definition are any glass, any metal capable of oxidation, or any metal oxide. The preferred metals are copper, chromium, aluminum, and titanium. The term "glass" includes silicon, silica, silicates, and fused mixtures of silicates of alkali and alkaline earth or heavy metals.

EXAMPLE 1

Preparation of N-3-(triethoxysilyl)propyl Benzocyclobutene 3-Carboxamide

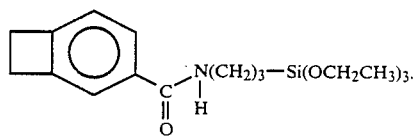

This reaction is carried out in a 100 milliliter (ml) round bottom three-neck flask equipped with magnetic stirring, a reflux condenser supplied with a positive nitrogen pressure via a mineral oil bubbler, a thermometer, and an addition funnel. 9.97 Grams (g) aminopropyl triethoxy silane (45.1 mmoles, vacuum distilled before use), 5.0 g triethylamine (49.5 mmoles) and 40 ml methylene chloride are added to the flask. This mixture is cooled with an external ice bath. 7.5 Grams benzocyclobutene 3-acid chloride (45.1 mmoles) is added dropwise through the addition funnel while stirring the cooled mixture. A white precipitate is formed. After this time, the ice bath is removed and the mixture is stirred overnight. The precipitate is removed by vacuum filtration and washed with 100 ml methylene chloride. 150 Milliliters pentane is then added to this solution to force further precipitation, and the precipitate is removed via filtration (total recovered triethylamine hydrochloride 6.2 g, theoretical 100 percent yield 6.2 g). The methylene chloride/pentane is then removed via rotary evaporation, leaving an orange/red oil. G.C. analysis[1] shows little remaining starting materials and the formation of a single new peak. The compound is purified by flash chromatography using a 50:50 v/v heptane/methyl ethyl ketone eluent mixture and 150 g 60-200 mesh silica gel. The recovered product is concentrated via rotary evaporation, and further devolatilized with a Kugelrohr apparatus for 2 hours at 90° C., 0.1 mm Hg. The recovered product is a light brown oil, clear, weighing 13.88 g (88 percent of theory).

IR[2], neat film on KBr 3320 cm$^{-1}$, 2980 cm$^{-1}$, 2920 cm$^{-1}$, 2880 cm$^{-1}$, 1640 cm$^{-1}$, 1600 cm$^{-1}$, 1540 cm$^{-1}$, 1470 cm$^{-1}$, 1430 cm$^{-1}$, 1390 cm$^{-1}$, 1295 cm$^{-1}$, 1165 cm$^{-1}$, 1100 cm$^{-1}$, 1080 cm$^{-1}$, 960 cm$^{-1}$, 790 cm$^{-1}$. H$^1$NMR[3], 300 MHz, CDCl$_3$ vs. TMS; 0.75 ppm, 2 H,t; 1.2 ppm, 9 H,t; 1.75 ppm, 2 H,m; 3.4 ppm, 2 H,m; 3.18, 4 H,s; 3.8 ppm, 6 H,q; 6.6 ppm, 1 H,s; 7.05 ppm, 1 H,d; 7.45 ppm, 1 H,s; 7.6 ppm, 1 H,d. C$^{13}$ NMR, CDCl$_3$, 75 MHz, chemical shifts vs. TMS; 7.92, 18.3, 22.9, 28.3, 29.6, 42.2, 58.4, 120.9, 122.2, 125.7, 133.8, 149.2, 145.6, 167.9. Capillary G.C., 15 meter 0.1 μm DB-1 coating, He at 10 psi, peak at 13.74 minutes, 8.55 area percent, peak at 14.77 minutes, 91.45 area percent.

[1] G.C. analysis is performed using a Hewlett-Packard 5710A Gas Chromotograph equipped with a DB-1 0.1 μm coated 15 meter column with a flame ionization detector and a Hewlett-Packard 3390A integrator.

[2] IR spectra is obtained using a Perkin-Elmer model 683 Infrared Spectrometer.

[3] NMR spectra is obtained using a Varian VXR 300 Nuclear Magnetic Resonance spectrophotometer. NMR spectra is run in dueterochlorform and chemical shifts are reported as compared to a tetramethylsilane internal standard.

EXAMPLE 2

Preparation of E[1-Triethoxysilyl 2-(3-Benzocyclobutenyl)]Ethylene

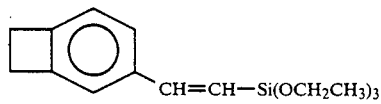

This reaction is carried out in a 100 ml round bottom three-neck flask which is equipped with magnetic stirring, a reflux condenser, a gas inlet tube which is used to supply a positive pressure of nitrogen to the reactor, a thermometer, and a stopper. To this flask is added 0.25 g Pd(O$_2$CCH$_3$)$_2$ (1.1 mmoles), 1.2 g tri-o-tolyl phosphine (3.9 mmoles), 6 g triethylamine (60 mmoles), 10.5 g triethoxy vinylsilane (55.2 mmoles), and 10 g 3-bromobenzocyclobutene (54.6 mmoles). The flask is equipped with a heating mantle and the contents are diluted with 50 ml acetonitrile. The mixture is heated to reflux with stirring, and the progress of the reaction is followed by removing samples hourly and analyzing for starting material by G.C. After 5 hours at reflux the reaction mixture is removed from the heat and allowed to cool to room temperature. The precipitate which forms during the reaction is removed via vacuum filtration and washed with 2×50 ml acetonitrile. The acetonitrile/triethylamine is removed in vacuo and the resultant oil is purified by short path distillation. The majority of the product is collected between 116° and 125° C., at ca 0.5 mm Hg. Recovered product after purification weights 22.8 g, or 71.5 percent of theory. IR, neat film of KBr; 2960 cm$^{-1}$, 2920 cm$^{-1}$, 1600 cm$^{-1}$, 1470 cm$^{-1}$, 1390 cm$^{-1}$, 1200 cm$^{-1}$, 1130 cm$^{-1}$, 1060-1100 cm$^{-1}$ (broad), 1000 cm$^{-1}$, 960 cm$^{-1}$, 830 cm$^{-1}$, 800 cm$^{-1}$, 789 cm$^{-1}$. H$^1$NMR, 300 MHz, in CDCl$^3$, chemical shifts vs. TMS; 1.2 ppm, t, J=7.2 Hz; 3.1 ppm, s; 3.7 ppm, q, J=72 Hz; 5.9-5.96, d, J=18.8 Hz; 7.0-7.4 ppm, m. C$^{13}$ NMR, in CDCl$_3$, 75 MHz, chemical shifts vs. TMS; 18.1, 29.1, 29.3, 58.3, 115.6, 119.9, 122.2, 126.15, 145.68, 146.5.

EXAMPLE 3

Preparation of N-Phenyl (o,m,p) Trimethoxysilyl Benzocyclobutene 3-Carboxamide

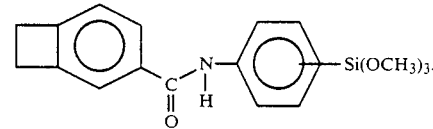

This reaction is run in a 100 ml three-neck round bottom flask equipped with magnetic stirring, a reflux condenser topped with a gas inlet adapter and supplied with a positive pressure of nitrogen, a thermometer, and a stopper. To this flask is added 40 ml methylene chloride and 5 g triethylamine. This mixture is cooled with a dry ice/acetone bath to 78° C. and evacuated to ca 10 mm Hg. The bath is then removed and the mixture is allowed to warm to 0° C., after which the vessel is refilled with nitrogen. The apparatus is then equipped with an addition funnel, and the round bottom flask is added 9.6 g aminophenyl trimethoxy silane (mixed isomers, 45 mmoles, from Petrarch Systems, distilled at reduced pressure before use and handled under nitrogen). The addition funnel is then charged with 10 ml methylene chloride and 7.5 g benzocyclobutene 3-acid chloride (45.1 mmoles). The flask is cooled with an ice water bath to <5° C., and the acid chloride solution is added over a 15 minute period, keeping the temperature below 15° C. A precipitate forms almost immediately upon addition. The ice bath is then removed, and the mixture is allowed to stir overnight. After this time the solvent is removed via rotary evaporation leaving an off white semisolid. The solid is then loaded onto a 1 inch. diameter chromatography column with 100 g silica gel and is eluted with a 50/50 v/v methyl ethyl ketone/heptane mixture. An initial fraction containing ca 300 ml eluant is concentrated via rotary evaporation to give a clear brown oil, weighing 3.5 g (25 percent of theory). This material is analyzed by IR, NMR methods.

IR KBr; 3300-3400 cm$^{-1}$, 2920 cm$^{-1}$, 1650 cm$^{-1}$, 1600 cm$^{-1}$, 1570 cm$^{-1}$, 1520 cm$^{-1}$, 1470 cm$^{-1}$, 1430 cm$^{-1}$, 1300 cm$^{-1}$, 1240 cm$^{-1}$, 1140-1100 cm$^{-1}$ (broad, 820 cm$^{-1}$, 760 cm$^{-1}$, 500 cm$^{-1}$, H$^1$NMR, 300 MHz, in CDCl$_3$; 3.16 ppm, s; 3.60 ppm, s; 7.0 ppm, s; 7.3-7.9, m.

$C^{13}$, 75 MHz in $CDCl_3$, chemical shifts vs. TMS; 29.35, 29.4, 50.8, multiple peaks for ring isomers of aminophenylsilane group; benzocyclobutene ring carbons 121.1, 122.5, 126.0, 133.0, 146.0 and 150.1; carbonyl at 166.6.

EXAMPLE 4

Copper to Copper Adhesion

For each of a series of runs, hot degassed monomer is poured into a mold. Each of the two opposing surfaces of the mold have a 1 oz. copper foil strip placed on an aluminum plate. The copper foil strip is obtained from the Foil Division of Gould Inc. Each opposing surface of the copper strip has been treated to prevent oxidation. The mold apparatus is placed into an air operated press (ca 80 psig) heated with pencil heaters. The mold is heated to 165° C., monomer is added, and the following heat cycle is used; 165° to 200° C. (10 minutes), 200° C. (1 hour), 200° C. to 235° C. (1 hour), 235° C. to 250° C. (2.5 hours), 250° C. to 275° C. (25 minutes), 275° C. (5 hours), and 275° C. to 200° C. (1.25 hours). The heater is then turned off and the mold is allowed to cool to room temperature. A copper clad plaque is removed from the mold apparatus (1 in. × 4 in. × ⅛ in.). A one half inch copper line is etched into the copper clad plaque by covering the copper with a ½ in. strip of scotch tape and then suspending the plaque in a $FeCl_3$ solution (100 gm $FeCl_3$-hexahydrate in 1-liter distilled water) for 0.5 to 1.5 hours, depending upon the age of the solution, until all of the excess copper has been removed. Adhesion strength of the copper foil for each run is determined. The results appear in Table I.

tion is allowed to sit overnight, after which it is filtered through a 0.2 μm filter.

For each of a series of runs, a Si wafer is heated in an oven for 30 minutes at 200° C. The wafer is removed from the oven and allowed to cool to room temperature. The wafer is then washed with either filtered xylene or methanol and xylene. The BCB-Silane solution is applied to the surface of the wafer, and the wafer is then spun at 6000 rpm for 30 seconds (ramp=400) in order to prepare a thin coating. The treated wafer is heated at 150° C. for 30 minutes. A prepolymer prepared from a preferred monomer of this invention is then dissolved in xylene to prepare a 35 percent solids solution. The prepolymer solution is applied to the surface of the treated wafer, and the wafer is then spun at 6000 rpm for 30 seconds (ramp=400) in order to prepare a thin prepolymer coating. After spinning, the wafer is purged under nitrogen for ten minutes. The prepolymer coating is cured by heating to 220° C., pausing at this temperature for 15 minutes, and then heating to 250° C. for one hour.

The adhesion of the cured coating is determined by applying adhesive tape to the surface of the coating and then removing the tape while keeping it at a 90° angle with respect to the coated surface. If the coating remains adhered to the surface, then the coated wafer is boiled in water for one hour and the adhesion is retested. The adhesion of the coating is compared to the adhesion of a coating on a wafer that has not been treated with a BCB-Silane. The results appear in Table II.

TABLE I

Peel Strength Comparison of Copper to Copper Using a BCB Resin Matrix With and Without BCB-Silane

| | Peel Strength[2], lbs/in of Width | | | |
|---|---|---|---|---|
| | Standard Copper[3] | | PI Copper[4] | |
| MONOMER[1] | Without BCB-Silane | With BCB-Silane[5] | Without BCB-Silane | With BCB-Silane[5] |
| 4 | 5.72 | 6.80 | 6.38 | 7.10 |
| 5 | 3.61 | 4.51 | 3.82 | 4.87 |
| 6 | 3.95 | 4.78 | 4.66 | 5.45 |
| Mixture: | | | | |
| Ninety-five weight percent 4 | 6.47 | 9.02[6] | 7.92 | 9.46[6] |
| Five weight percent 5 | | 9.77[7] | | 9.68[7] |

[1]Column numbers represent monomers disclosed as Formulas 4, 5 and 6, respectively, in the specification
[2]Determined by conducting 90° peel tests using a 1127 Instron Universal Testing Machine with a cross head speed of 2 in/min and a full scale reading of 5 kg.
[3]Standard copper foil pretreated for use with epoxy resins, sold commercially by Gould, Inc.
[4]Copper foil specifically pretreated for use with polyimide resins, sold commercially by Gould Inc.
[5]BCB-Silane disclosed as Formula I in the specification. For Monomers 4 and 5, BCB-Silane applied by coating a solution of 0.1 gm BCB-Silane in 0.1 gm hexane on pretreated foil surface and then evaporating hexane. For monomer 6, BCB-Silane applied by adding 0.5 weight percent BCB-Silane directly to monomer before cure. Weight percent based on total weight of monomer and BCB-Silane.
[6]BCB-Silane applied by same method as method used for monomer 6.
[7]BCB-Silane applied by same method as method used for monomers 4 and 5.

The date indicate significantly improved adhesion of the matrix resin to copper when a BCB-silane is used relative to the adhesion demonstrated when a BCB-Silane is not used. In some cases, a 50 percent increase in adhesion is observed. The improvements are obtained regardless of the method of application.

EXAMPLE 5

Polymer to Silicon

A 0.1 percent BCB-Silane solution is prepared by adding 0.021 g of E[1-triethoxysilyl-2-(3-benzocyclobutenyl)]ethylene (0.072 mmoles) to 19.98 g of a 95 percent methanol/5 percent water mixture. The solu-

TABLE II

Adhesion Comparsion of a Polymer Derived From a BCB Resin Matrix To Either an Untreated Silicon Wafer or a Silicon Wafer Treated With a BCB-Silane

| | Adhesion | |
|---|---|---|
| Monomer[1] | Without BCB-Silane | With BCB-Silane[2] |
| 5 | good[3] | excellent[4] |
| 6 | good | excellent |
| bis E-(3-benzocyclobutenyl)- | good | excellent |

TABLE II-continued

Adhesion Comparsion of a Polymer Derived From a
BCB Resin Matrix To Either an Untreated Silicon
Wafer or a Silicon Wafer Treated With a BCB-Silane

| Monomer[1] | Adhesion | |
|---|---|---|
| | Without BCB-Silane | With BCB-Silane[2] |
| ethylene[5] | | |

[1] Column numbers represent monomers disclosed as Formulas 5 and 6, respectively.
[2] BCB-Silane disclosed as Formula I in the specification.
[3] Good adhesion designates an intital pass on the 90° tape pull test but a fail after the water boil.
[4] Excellent adhesion designates a pass on the 90° tape pull test both before and after the water boil.

What is claimed is:

1. A method of increasing adhesion between an inorganic surface and a polymer, comprising the steps of:
   (a) contacting the inorganic surface with a homogeneous mixture of: (1) a monomer or prepolymer precursor of the polymer, and (2) an effective amount of an organosilane adhesion aid of the formula:

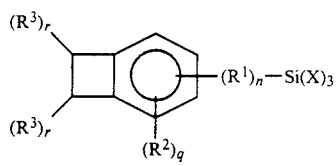

wherein
   $R^2$ is —CH=CH—Y— or

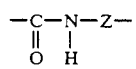

and
   Y is a direct bond, phenylene of $(CH_2)_m$,
   Z is phenylene of $(CH_2)_m$;
   m is an integer between 1 and 4, inclusive;
   $R^2$ is $C_{1-4}$ alkyl, methoxy, methoxycarbonyl, trifluoromethoxycarbonyl, nitro, or halo;
   each $R^3$ is independently $C_{1-4}$ alkyl, halo, nitro, or cyano;
   X is $C_{1-4}$ alkoxy;
   n is 0 or 1; and
   each q and r is independently 0 or 1; and then
   (b) polymerizing the monomer or prepolymer while maintaining contact between the mixture and the inorganic surface.

2. The method of claim 1 wherein the organosilane adhesion aid has the formula:

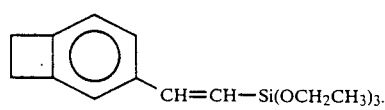

3. The method of claim 1 wherein the organosilane adhesion aid has the formula:

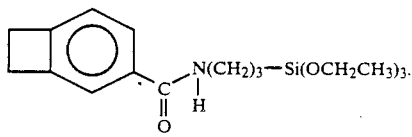

4. The method of claim 1 wherein the organosilane adhesion aid has the formula:

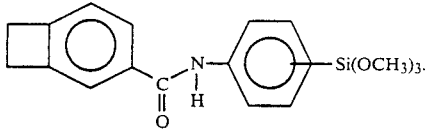

5. The method of claim 1 wherein the amount of the organosilane adhesion aid in the mixture is about 0.01 to about 20 percent of the weight of the mixture.

6. The method of claim 1 wherein the inorganic surface is the surface of a glass, a metal capable of oxidation, or a metal oxide.

7. The method of claim 6 wherein the monomer or prepolymer precursor is derived from benzocyclobutene.

8. The method of claim 7 wherein the monomer has the formula:

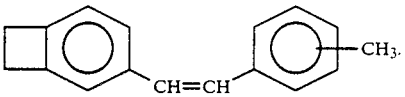

9. The method of claim 7 wherein the monomer has the formula:

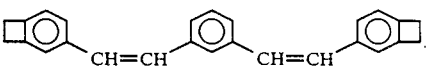

10. The method of claim 7 wherein the monomer has the formula:

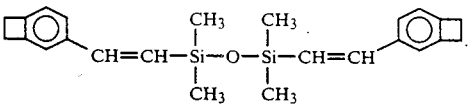

11. The method of claim 7 wherein the monomer has the formula:

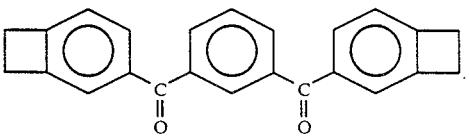

12. A method of increasing adhesion between an inorganic surface and a polymer, comprising the steps of:
   (a) dissolving an effective amount of an organosilane adhesion aid of the formula:

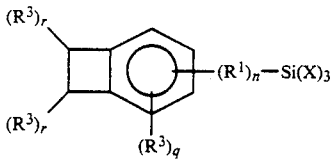

wherein
R¹ is —CH=CH—Y— or

—C—N—Z—
‖ |
O H and
Y is a direct bond, phenylene or $(CH_2)_m$,
Z is phenylene or $(CH_2)_m$,
m is an integer between 1 and 4, inclusive;
R² is $C_{1-4}$ alkyl, methoxy, methoxycarbonyl, trifluoromethoxycarbonyl, nitro, or halo;
each R³ is independently $C_{1-4}$ alkyl, halo, nitro, or cyano;
X is $C_{1-4}$ alkoxy;
n is 0 or 1; and
each q and r is independently 0 or 1; in a suitable solvent so as to prepare a solution,
(b) applying an amount of the solution to the inorganic surface sufficient to wet the surface,
(c) removing substantially all of the solvent from the applied solution,
(d) contacting a monomer or prepolymer precursor of the polymer with the wetted inorganic surface, and then
(e) polymerizing the monomer or prepolymer while maintaining contact between the monomer or prepolymer and the wetted inorganic surface.

13. The method of claim 12 wherein the monomer or prepolymer precursor is a solution of the monomer or prepolymer in an organic solvent.

14. The method of claim 13 wherein the organic solvent is xylene, THF, or toluene.

15. The method of claim 14 wherein the organic solvent is xylene or THF.

16. The method of claim 12 wherein the organosilane adhesion aid has the formula:

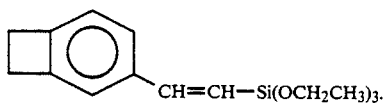

17. The method of claim 12 wherein the organosilane adhesion aid has the formula:

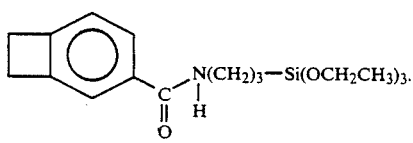

18. The method of claim 12 wherein the organosilane adhesion aid has the formula:

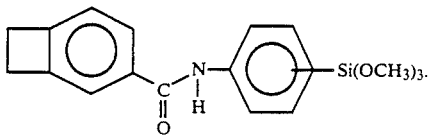

19. The method of claim 12 wherein the solvent for the organosilane adhesion aid is an aqueous solution of a $C_{1-4}$ alcohol or an organic solvent selected from the group consisting of xylene, THF, toluene, heptane, hexane, acetone, and methylene choride.

20. The method of claim 19 wherein the amount of organosilane adhesion aid in the aqueous solution of a $C_{1-4}$ alcohol is about 0.1 to about 1 percent of the weight of the solution.

21. The method of claim 20 wherein the $C_{1-4}$ alcohol is methanol or ethanol.

22. The method of claim 19 wherein the organic solvent is xylene or THF.

23. The method of claim 12 wherein the inorganic surface is the surface of a glass, a metal capable of oxidation, or a metal oxide.

24. The method of claim 23 wherein the monomer or prepolymer precursor is derived from benzocyclobutene.

25. The method of claim 24 wherein the monomer has the formula:

26. The method of claim 24 wherein the monomer has the formula:

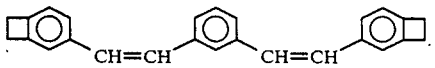

27. The method of claim 24 wherein the monomer has the formula:

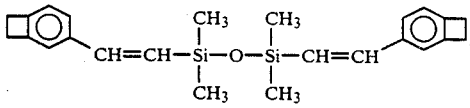

28. The method of claim 24 wherein the monomer has the formula:

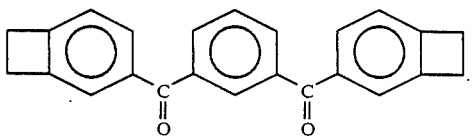

* * * * *

UNITED STATES PATENT AND TRADEMARK OFFICE
CERTIFICATE OF CORRECTION

PATENT NO. : 5,002,808

DATED : March 26, 1991

INVENTOR(S) : Stephen F. Hahn and Dennis J. Kreil

It is certified that error appears in the above-identified patent and that said Letters Patent is hereby corrected as shown below:

Column 11, Claim 1, line 37, " $R^2$ is -CH=CH-Y- or " should correctly read -- $R^1$ is -CH=CH-Y- or --.

Column 11, Claim 1, line 45, " phenylene of $(CH_2)_m$ " should correctly read -- phenylene or $(CH_2)_m$ --.

Column 11, Claim 1, line 46, " Z is phenylene of $(CH_2)_m$ " should read -- Z is phenylene or $(CH_2)_m$ --.

Signed and Sealed this

Twenty-ninth Day of December, 1992

*Attest:*

DOUGLAS B. COMER

*Attesting Officer*  Acting Commissioner of Patents and Trademarks